US009176148B2

(12) United States Patent
Devarajan

(10) Patent No.: US 9,176,148 B2
(45) Date of Patent: Nov. 3, 2015

(54) METHOD FOR THE EARLY DETECTION OF RENAL DISEASE USING PROTEOMICS

(71) Applicant: Children's Hospital Medical Center, Cincinnati, OH (US)

(72) Inventor: Prasad Devarajan, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 259 days.

(21) Appl. No.: 14/044,953

(22) Filed: Oct. 3, 2013

(65) Prior Publication Data

US 2014/0080166 A1 Mar. 20, 2014

Related U.S. Application Data

(63) Continuation of application No. 11/379,481, filed on Apr. 20, 2006, now abandoned.

(60) Provisional application No. 60/673,453, filed on Apr. 21, 2005.

(51) Int. Cl.
*G01N 33/53* (2006.01)
*G01N 33/68* (2006.01)

(52) U.S. Cl.
CPC ........ *G01N 33/6893* (2013.01); *G01N 33/6842* (2013.01); *G01N 33/6848* (2013.01); *G01N 33/6851* (2013.01); *G01N 2800/226* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 4,444,879 A | 4/1984 | Foster et al. | |
| 6,447,989 B1 | 9/2002 | Comper | |
| 6,579,719 B1 | 6/2003 | Hutchens et al. | |
| 6,811,689 B2 | 11/2004 | Zhang et al. | |
| 6,811,969 B1 | 11/2004 | Hutchens et al. | |
| 6,814,870 B2 | 11/2004 | Zhang et al. | |
| 6,818,411 B2 | 11/2004 | Hutchens et al. | |
| 6,844,165 B2 | 1/2005 | Hutchens et al. | |
| 6,881,586 B2 | 4/2005 | Hutchens et al. | |
| 7,105,339 B2 | 9/2006 | Hutchens et al. | |
| 7,141,382 B1 | 11/2006 | Parikh et al. | |
| 7,191,068 B2 | 3/2007 | Rosenfeld et al. | |
| 7,341,838 B2 | 3/2008 | Buechler et al. | |
| 7,605,003 B2 | 10/2009 | Chan et al. | |
| 2002/0142284 A1 | 10/2002 | Raha et al. | |
| 2003/0219734 A1 | 11/2003 | Buechler | |
| 2004/0029192 A1 | 2/2004 | Shaw et al. | |
| 2004/0137427 A1 | 7/2004 | Hutchens et al. | |
| 2004/0197930 A1 | 10/2004 | Rosenfeld et al. | |
| 2004/0219603 A1 | 11/2004 | Devarajan et al. | |
| 2004/0253636 A1 | 12/2004 | Soloviev et al. | |
| 2005/0048566 A1 | 3/2005 | Delisi et al. | |
| 2005/0059013 A1 | 3/2005 | Chan et al. | |
| 2005/0064511 A1 | 3/2005 | Buechler et al. | |

FOREIGN PATENT DOCUMENTS

WO  WO 2004/005544    1/2004
WO  WO 2004088276  * 10/2004

OTHER PUBLICATIONS

Pieper et al. (Proteomics 2004 vol. 4, p. 1159-1174; Table 1).*
Ahlstrom, et al, Clinical Nephrol, Nov. 2004, vol. 62(5), pp. 344-350.
Cadieux, P., "SELDI-TOF-MS: a new proteomic urinary test for patients with urolithiasis," J. Clin. Lab. Anal., 2004, vol. 18(3), pp. 170-175.
Corso, et al, Ann. Hematol., 1999, vol. 78, pp. 371-375.
Cutillas, et al, News Physiol Sci, 2004, vol. 19, pp. 114-119.
Fauli, A., et al, "Kidney-specific proteins in patients receiving aprotinin at high- and low-dose regimens during coronary artery bypass graft with cardiopulmonary bypass," European Journal of Anesthesiology, Jun. 2005, vol. 22, pp. 666-671.
Fournier, et al, Biochimica et Biophysica Acta, 2000, vol. 1482, pp. 157-171.
Jain, S., et al, "Proteomic Analysis of urinary Protein Markers for Accurate Prediction of Diabetic Kidney Disorder," JAPI, Jun. 2005, vol. 53, pp. 513-520.
Kostner, et al, Clinica Chimica Acta, 2001, vol. 304, pp. 29-37.
Kumar, Y., et al, "Proteomics of renal disorders; Urinary proteome analysis by two-dimensional gel electrophoresis and MALDI-TOFF mass spectrometry," Current Science, Mar. 25, 2002, vol. 82, No. 6, pp. 655-663.
Kwon, et al, American Journal of Kidney Disease, 2003, vol. 41(5), pp. 1074-1087.

(Continued)

*Primary Examiner* — Jacob Cheu
(74) *Attorney, Agent, or Firm* — Frost Brown Todd LLC

(57) ABSTRACT

A method for the detection of an early biomarker for assessing a change in renal status in a mammalian subject following a renal event. The method typically includes the steps of (a) providing a body fluid sample obtained from a mammalian subject; (b) analyzing the molecular weight of the proteins in the sample using proteome analysis; and (c) identifying the presence of a protein in the sample selected from the group consisting of a 6.4 kDa protein, a 28.5 kDa protein, a 33 kDa protein, a 44 kDa protein, a 67 kDa protein, and combinations thereof. The presence of one of these proteins can serve as an early biomarker for assessing a change in renal status. The levels of these proteins can be compared to predetermined levels, and thus provide a determination of the subject's renal status. The invention also includes a method of assessing the administration of aprotinin during cardio-pulmonary bypass surgery and provides for methods where the level of the 6.4 kDa biomarker in the subject's urine directs a caregiver's therapeutic decision regarding the intra-operative administration of aprotinin.

12 Claims, 10 Drawing Sheets

(56) References Cited

OTHER PUBLICATIONS

Mishra, J., et al, "Neutrophil gelatinase-associated lipocalin (NGAL) as a biomarker for acute renal injury after cardiac surgery," Lancet, Apr. 2005, vol. 365, pp. 1231-1238.

Nguyen, M., et al, "Early Prediction of Acute Renal Injury Using Urinary Proteomics," American Journal of Nephrology, 2005, vol. 25, pp. 318-326.

Schaub, S., et al, "Proteomic-Based Detection of Urine Proteins Associated with Acute Renal Allograft Rejection," J. Am. Soc. Nehprol., 2004, vol. 15, pp. 219-227.

Schweigert, et al, Proteome Science, 2004, vol. 2, pp. 1-6.

Tabatabai, L.B., "Using Proteomics in Diagnostics," In Vitro Diagnostic Technology, 2008, vol. 8(7), pp. 37-48.

\* cited by examiner

METHOD FOR THE EARLY DETECTION OF RENAL DISEASE USING PROTEOMICS

CROSS-REFERENCE TO RELATED APPLICATION

This application is a continuation of U.S. application Ser. No. 11/379,481 filed on Apr. 20, 2006, which claims the benefit of U.S. Provisional Patent Application No. 61/673,453 filed Apr. 21, 2005, all of which are incorporated by reference in their entirety for all purposes.

This invention was made with government support under DK070163, DK052612 and DK053289 awarded by the National Institutes of Health. The government has certain rights in the invention.

FIELD OF THE INVENTION

The present invention relates generally to a method of determining the renal status of a subject, and in particular to a method of determining early impaired renal status and nephrotoxicity in a subject.

BACKGROUND OF THE INVENTION

Early detection of disease states in mammals has been the focus of much recent research. For disease detection, the public-health community has historically relied on laboratory tests that can sometimes take days or even weeks to return a result. The increased availability of better and faster diagnostic tests, however, promises the possibility of more automated and earlier disease detection and subsequent intervention. It is believed that introduction of therapy early in the disease process will reduce the mortality rate associated with the disease and shorten the time for treatment.

Acute renal failure (ARF) secondary to renal injury, including but not limited to ischemic injury and nephrotoxic injury, remains a common and potentially devastating problem in clinical nephrology. Five percent (5%) of hospital admissions and 30% of Intensive Care Unit admissions have acute renal failure, and 2-5% of hospitalized patients will develop it. Acute renal dysfunction occurs in up to 40% of adults following cardiac surgery. Pathophysiologic mechanisms include diminished renal blood flow, loss of pulsatile flow, hypothermia, atheroembolism, and a generalized inflammatory response. ARF requiring dialysis also complicates up to 10% of cardiac surgeries in infants and children with congenital heart disease.

ARF persistently continues to result in a high rate of mortality despite significant advances in supportive care. Pioneering studies over several decades have illuminated the roles of persistent vasoconstriction, tubular obstruction, cellular structural and metabolic alterations, and the inflammatory response in the pathogenesis of ARF. While these studies have paved the way for successful therapeutic approaches in animal models, translational research efforts in humans have yielded disappointing results, for reasons such as the multi-faceted response of the kidney to ischemic injury and a paucity of early markers for ARF with a resultant delay in initiating therapy.

Animal studies have shown that, while ARF due to ischemia can be prevented and/or treated by several maneuvers, treatment for ARF must be instituted very early after the ischemic insult. A major reason for the inability to provide preventive and therapeutic measures for ARF in humans is the lack of early biomarkers for ARF. Thus, the identification of a reliable, early biomarker for impaired renal status would be useful to facilitate early therapeutic intervention, and help guide pharmaceutical development by providing an early indicator of nephrotoxicity.

The traditional laboratory approach for detection of renal disease involves determining the serum creatinine, blood urea nitrogen, creatinine clearance, urinary electrolytes, microscopic examination of the urine sediment, and radiological studies. These indicators are not only insensitive and nonspecific, but also do not allow for early detection of the disease. In current clinical practice, ARF is typically diagnosed by measuring a rise in serum creatinine over time, which is an unreliable indicator for measuring acute changes in kidney function. Indeed, while a rise in serum creatinine is widely considered as the "gold standard" for the detection of ARF, it is a late indicator of renal injury since as much as 50% of the kidney function may already be lost by the time the serum creatinine changes. Currently there are no tools available for the early diagnosis of impaired renal status.

The lack of early biomarkers for acute renal injury thus has severely slowed progress in finding effective therapies within the narrow window of opportunity. The identification of urinary protein biomarkers suitable for the early detection and diagnosis of acute renal injury holds great promise to improve the clinical outcome of patients. It is especially important for patients presenting with vague or no symptoms or with acute renal injury following surgery such as cardio-pulmonary bypass surgery. Despite considerable effort directed at early detection of ARF, no cost-effective screening tests have been developed to date.

Although efforts to evaluate disease processes and drug effects have traditionally focused on genomics, more attention has been paid recently to proteomics due to its offering a more direct, complete and promising understanding of the biological functions of a cell. The term "proteomics" was coined to make an analogy with genomics, and while it is often viewed as a continuation of genomics, proteomics is much more complicated than genomics. Most importantly, whilst the genome is a rather constant entity, the proteome differs from cell to cell and is constantly changing through its biochemical interactions with the genome and the environment. One organism will have radically different protein expression in different parts of its body, in different stages of its life cycle and in different environmental conditions.

The protein map of a biological system, including a cell, sub-cellular fraction or expression media, can be referred to as a proteome. Proteomics, or analysis of the proteome of a biological system, offers a relatively new approach to protein expression profiling and cellular or tissue protein identification from samples that are obtained under various specified conditions. Proteomics has an enormous breadth of application ranging from investigation and identification of biomarkers, molecules that are indicative of a particular pathological state, which in turn can be used for diagnostic purposes and targets for therapeutic intervention. Proteome analysis allows the investigator to obtain information on protein identity, protein-protein interaction, the level of protein expression and protein expression profiling, protein trafficking and turnover, protein variants, and protein post-translational modifications.

Traditionally, proteomics combines two-dimensional electrophoresis (2-DE), a high-resolution protein separation technique, with mass spectrometry (MS). Proteomics research is targeted towards characterization of the proteins encoded by a particular genome and its changes under the influence of biological stimulation. Proteomics also involves the study of non-genome encoded events such as the post-translation modification of proteins, interactions between proteins, and the location of proteins within the cell. The study of gene expression at the protein level is important because many of the most important cellular activities are directly regulated by proteins in the cell rather than by gene activity. Also, the protein content of a cell is highly relevant to drug discovery and drug development efforts since most drugs are designed to target proteins. Therefore, the information gained from proteomics is expected to greatly boost the number of drug targets.

Attempts at unraveling the molecular basis of early renal responses have been facilitated by recent advances in functional genomics that have yielded new tools for genome-wide analysis of complex biologic processes. To date, the most popular method for proteomics investigation is the use of high-resolution two-dimensional gel electrophoresis and sensitive mass spectrophotometry techniques. Although two-dimensional gel electrophoresis is one of the most powerful methods in the current study of proteomics, this method is labor-intensive, time consuming, and limited in sensitivity. The two-dimensional gel electrophoresis method also suffers from poor reproducibility. To avoid the aforementioned disadvantages of two-dimensional gel electrophoresis, microchip-based separation devices (microarrays) have been developed for rapid analysis of large numbers of samples. Compared to conventional separation columns or devices, microarrays have higher sample throughput, reduced sample and reagent consumption, and reduced chemical waste. Such devices are capable of fast analyses and provide improved precision and reliability compared to the conventional analytical instruments. The cDNA microarray methodologies provide parallel and quantitative expression profiles of thousands of genes, which when combined with bioinformatics tools, can identify genes in a biologic pathway, characterize the function of novel genes, and detect disease subclasses. However, until now, no early stage molecular markers have been identified for ARF.

Mass spectrometry is a technique that measures m/z (mass-to-charge) intensity pairs of an ionizable substance. The m/z-intensity pair or pairs of an analyte provides a signature distinguishing the analyte from other substances having a different m/z-intensity pair or pairs. The intensity of an analyte's m/z-intensity pair changes with the analyte's abundance within the response range of the instrument. Techniques and equipment for generating mass spectrometry data are well known in the art. Examples of ionization techniques that can be employed include electrospray ionization, matrix-assisted laser desorption/ionization (MALDI), surface enhanced laser desorption/ionization (SELDI), electron impact ionization, chemical ionization, and photoionization.

Recently, a chip-based proteomics approach has been introduced using biomolecular interaction analysis-mass spectrometry (BIA-MS) in rapidly detecting and characterizing proteins present in complex biological samples at very low levels. One of the most powerful techniques is Surface Enhanced Laser Desorption/Ionization Time-of-Flight Mass Spectrometry (SELDI-TOF-MS) technology, which has been commercially embodied in Ciphergen's ProteinChip® Biomarker System. The system uses chemically (cationic, anionic, hydrophobic, metal, etc.) or biochemically (antibody, DNA, enzyme, receptor, etc.) treated surfaces for specific interaction with proteins of interest, followed by selected washes for SELDI-TOF-MS detection. Surface-Enhanced Laser Desorption/Ionization (SELDI) was invented in the late 1980's. When coupled to a time-of-flight mass spectrometer (TOF), SELDI provides a means to rapidly analyze molecules retained on a chip. The power of the system incorporates straightforward sample preparation with on-chip capture (binding) and detection for protein discovery, protein purification, and protein identification from small samples, allowing rapid analysis and assay development on a single platform.

Several tubular proteins have been measured in the urine, with conflicting and unsatisfactory results. For example, one cDNA microarray expression profile identifies kidney injury molecule-1 (KIM-1), a novel kidney-specific adhesion molecule involved in renal regeneration which is upregulated 24-48 hours after initial insult. KIM-1 is a reliable but somewhat late stage marker of tubular cell damage, and has been detected in the kidney biopsy and in the urine of patients with established ischemic acute tubular necrosis. However, this detection was documented in patients with established ischemic renal damage, late in the course of the illness. The utility of urinary KIM-1 measurement for the detection of early ARF or subclinical renal injury has thus far not been validated. Also, sodium-hydrogen exchanger isoform 3 (NHE-3) has been shown in the urine from subjects with established ARF. The sensitivity and specificity of these biomarkers for the detection or prediction of impaired renal status have not been reported. Of the inflammatory cytokines involved in ARF, elevated levels of urinary IL-6, IL-8 and IL-18 have been demonstrated in patients with delayed graft function following cadaveric kidney transplants. None of these biomarkers have been examined prospectively for their appearance in the urine during the evolution of ischemic ARF.

There is currently a lack of a reliable biomarker for the early determination of renal injury and disease caused by ischemia and/or nephrotoxicity. Therefore, it would be advantageous to provide testing of a subject's urine, blood serum, or other body fluid samples for early biomarkers of acute renal injury within minutes of a suspected injury, since early biomarkers for acute renal failure may begin to appear at low levels and continue to rise thereafter. It would likewise be advantageous if early biomarkers for acute renal injury could be detected in bodily fluid samples such as blood serum and urine shortly after the onset of a renal event that could lead to renal tubular cell injury. It would also be advantageous to use the ability of the SELDI-TOF-MS technology to rapidly identify protein biomarkers in a method of rapid identification of early biomarkers of various diseases, including ischemic and nephrotoxic renal injuries. There is also a need to provide a reliable and accurate method of early determination of the existence of acute renal injury in patients, the results of which can then be used to manage the treatment of affected patients.

SUMMARY OF THE INVENTION

The invention provides methods for the early detection of a change in renal status using proteomics. The invention typically uses SELDI-TOF-MS technology to rapidly identify early protein biomarkers of acute renal injury.

A first aspect of the invention provides a method for the detection of an early biomarker for assessing a change in renal status in a mammalian subject following a renal event, the method comprising the steps of (a) providing a body fluid sample obtained from a mammalian subject following a renal event; (b) analyzing the molecular weight of the proteins in the sample using proteome analysis; and (c) identifying the presence of a protein in the sample selected from the group consisting of a 6.4 kDa protein, a 28.5 kDa protein, a 33 kDa protein, a 44 kDa protein, a 67 kDa protein and combinations thereof, the presence of the protein serving as an early biomarker for assessing a change in renal status.

A second aspect of the invention provides a method for determining the renal status of a mammalian subject within 48 hours following a renal event, the method comprising the steps of (a) providing a body fluid sample obtained from a mammalian subject at a time within 48 hours following a renal event; (b) separating the proteins in the body fluid sample by molecular weight using proteome analysis; (c) identifying a separated protein based on the molecular weight of the separated protein, the separated protein being selected from the group consisting of a 6.4 kDa protein, a 28.5 kDa protein, a 33 kDa protein, a 44 kDa protein, a 67 kDa protein, and combinations thereof; and (d) comparing the level of each identified protein to a predetermined level thereof, the comparison providing a determination of the subject's renal status.

A third aspect of the invention provides a method for assessing the administration of aprotinin during cardio-pulmonary bypass surgery, the method comprising (a) providing a urine sample obtained from a subject receiving cardio-pulmonary bypass surgery; (b) separating the proteins in the sample by molecular weight using proteome analysis; (c) identifying the presence of a 6.4 kDa protein; and (d) comparing the level of the 6.4 kDa protein to a predetermined level thereof, wherein the comparison directs a caregiver's therapeutic decision regarding the intra-operative administration of aprotinin during cardio-pulmonary bypass surgery.

With the methods of the present invention, the body fluid sample is typically urine, blood, serum, plasma, saliva, lymph, cerebrospinal fluid, cystic fluid, ascites, stool, bile, and any isolatable body fluid, the renal event is typically diminished blood supply to the kidneys, sepsis, shock, trauma, kidney stones, kidney infection, impaired heart function, surgical procedures including cardio-pulmonary bypass surgery, admission of the subject into an intensive care unit, and the administration of medicament substances to the subject. The medicament substances can be pharmaceuticals, poisons or toxins, or iodinated contrast dyes.

The nature and advantages of the present invention will be more fully appreciated from the following drawings and detailed description.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

Figure 1A:
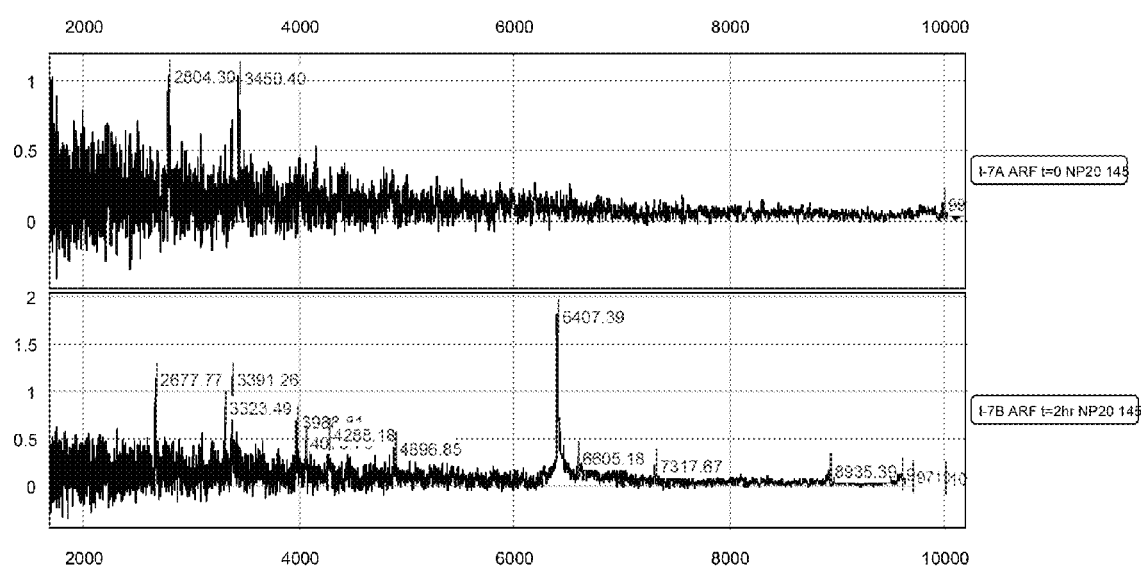
FIG. 1A is a graph showing representative SELDI-TOF-MS spectra of urine proteins in the 2,000-10,000 kDa range obtained from patients in the ARF group at baseline (top panel) and at 2 hours post-CPB (bottom panel).

The practice of the present invention will employ, unless otherwise indicated, conventional methods of nephrology, molecular biology and other laboratory techniques within the skill of the art.

Definitions

In describing the invention, and as used in this specification and the appended claims, the following terms and phrases will be employed, and are intended to be defined as indicated below.

The singular forms "a," "an" and "the" include plural references unless the content clearly dictates otherwise.

The term "biomarker" or "biomarkers" means a molecule or protein that is indicative of a particular pathological state.

The term "CPB" means cardio-pulmonary bypass surgery.

The phrase "change in renal status" means a variation or difference in an individual's renal status at one point in time as compared to another point in time.

The term "early" or "early on-set" in relation to a biomarker is a biomarker protein that can appear in the blood serum or urine within the first 24 hours, more typically within the first 4-6 hours, of the onset of injury.

The term "immediate" in relation to a renal tubular cell biomarker is a biomarker protein that can appear in the blood serum within 2 hours of the onset of renal tubular cell injury.

The phrase "impaired renal status" means a decline in renal function. For example, in an individual who previously had normal kidney function but has suffered renal injury, current renal status can be classified as normal, slightly impaired, moderately impaired, and severely impaired. Impaired renal status can be either sudden (acute) or slowly developing over time (chronic), and can be triggered by a number of disease or disorder processes. For acutely impaired renal status, triggers include (but are not limited to) cardiac surgery, other surgeries, kidney transplantation, shock, sepsis, trauma, stroke, kidney infection, and administration of nephrotoxins (such as radio-contrast agents, non-steroidal anti-inflammatory drugs (NSAIDs), antibiotics, and chemotherapeutic agents). For chronically impaired renal status, triggers include (but are not limited to) hypertension, diabetes, heart failure, lupus, sickle cell disease, and other inherited or acquired diseases of the kidney glomerulus or tubules. Both forms of impaired renal status can result in a life-threatening metabolic derangement.

The term "high amount" means an amount that is significantly higher as compared to a predetermined level.

The phrase "improved renal status" means an improvement in renal function. For example, in an individual who has received treatment for previously impaired renal status, current renal status can be classified as slightly improved, moderately improved, and greatly improved.

The term "increased amount" means an amount that is more as compared to a predetermined level.

"Managing subject treatment" refers to the behavior of the clinician or physician subsequent to the determination of the subject's renal status. As a non-limiting example, if the result of the methods of the present invention is inconclusive or there is reason that confirmation of status is necessary, the physician may order more tests. Alternatively, if the status indicates that treating for acute renal injury is appropriate, the physician may schedule the patient for the appropriate treatment. Likewise, if the status is negative (e.g., there is no indication of impaired renal status), no further action may be warranted. Furthermore, if the results show that treatment has been successful, no further management may be necessary.

The term "molecular weight" means the average molecular weight of a particular protein or biomarker that is measured, within a margin of error consistent with the measuring system being used. Experimental error and deviation should be allowed for. Unless indicated otherwise, molecular weight is molecular weight in kilodaltons (kDa).

The phrase "predetermined level" means (1) a known standard level as it pertains to levels found in samples from similar mammalian subjects; or (2) a level previously measured in a similar sample(s) from a particular mammalian subject.

The term "proteome" means the protein complement of the genome, or the protein map of a biological system.

The term "proteome analysis" means in general the analysis of the proteome of a biological system, typically from samples that are obtained under various specified conditions, and specifically relates to techniques known in the art for obtaining information about a biological sample including protein identity, protein-protein interaction, the level of protein expression and protein expression profiling, protein trafficking and turnover, protein variants, and protein post-translational modifications.

The term "renal event" means an incident with a high likelihood of affecting a mammalian subject's renal function and leading to a change in renal status. As a non-limiting example, renal events can include cardio-pulmonary bypass (CPB), renal hypoperfusion, hypovolemia, hemorrhage, systemic vasodilation, low cardiac output, hyperviscosity syndrome, renovascular obstruction, infection, and allergic reactions.

The term "renal status" means the condition or state of an individual's renal function. Generally the renal status is determined to be normal, impaired or improved, as compared to predetermined levels.

The term "sample" means a body fluid sample obtained from a mammalian subject, and can be urine, blood, serum, plasma, saliva, lymph, cerebrospinal fluid, cystic fluid, ascites, stool, bile, and any other isolatable body fluid.

The present invention provides a method for the early determination of a subject's renal status following a renal event or disease caused by ischemia and nephrotoxicity. The method utilizes proteome analysis techniques, such as urinary proteomics, including the SELDI-TOF-MS technique or similar proteome analysis technique for obtaining information on protein identity, protein-protein interaction, the level of protein expression, or protein expression profiling.

SELDI-TOF-MS provides a means to rapidly analyze molecules retained on a chip. The power of the system incorporates straightforward sample preparation with on-chip capture (binding) and detection for protein discovery, protein purification, and protein identification from small samples, allowing rapid analysis and assay development on a single platform. Of the various methods available in clinical proteomics, the ProteinChip® Biomarker System (SELDI-TOF-MS PBS-IIc) technology from Ciphergen has emerged as the preferred platform for protein profiling. Ciphergen's ProteinChip® system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation, baseline subtraction, high frequency noise filtering.

TOF-to-M/Z transformation involves the application of an algorithm that transforms times-of-flight into mass-to-charge ratio (m/z). In this step, the signals are converted from the time domain to the mass domain. That is, each time-of-flight is converted into mass-to-charge ratio, or m/z. Calibration can be done internally or externally. In internal calibration, the sample analyzed contains one or more analytes of known m/z. Signal peaks at times-of-flight representing these massed analytes are assigned the known m/z. Based on these assigned m/z ratios, parameters are calculated for a mathematical function that converts times-of-flight to m/z. In external calibration, a function that converts times-of-flight to m/z, such as one created by prior internal calibration, is applied to a time-of-flight spectrum without the use of internal calibrants.

Baseline subtraction improves data quantification by eliminating artificial, reproducible instrument offsets that perturb the spectrum. It involves calculating a spectrum baseline using an algorithm that incorporates parameters such as peak width, and then subtracting the baseline from the mass spectrum.

This approach allows for rapid high throughput profiling of multiple samples, detects low molecular weight biomarkers that are typically missed by other platforms, and even uncovers proteins bound to albumin. The quest for easily measured and reliable biomarkers is an area of intense contemporary research. However, regarding ischemic renal injury, the studies reported thus far have been retrospective and have examined biomarkers in the late, established phase of acute renal failure.

The method of the present invention identifies biomarkers for acute renal injury that are present in mammalian subjects soon after renal injury. The biomarkers are identified by distinguishing the protein profile in subjects experiencing impaired renal status or disease. Proteins in body fluid samples are defined by their mass-to-charge ratio (m/z), according to the assay used, typically a proteome analysis technique such as the SELDI-TOF-MS technique. Five early biomarkers for assessing a change in renal status are disclosed in accordance with the methods described herein. They are: (1) a 6.4 kDa protein, (2) a 28.5 kDa protein, (3) a 33 kDa protein, (4) a 44 kDa protein, and (5) a 67 kDa protein.

The methods of the present invention identify a plurality of proteins which are early biomarkers for assessing a change in renal status. The plurality of proteins comprises a 28.5 kDa protein, a 33 kDa protein, a 44 kDa protein, and a 67 kDa protein. In addition, when associated with the intra-operative administration of aprotinin during cardio-pulmonary surgery, a 6.4 kDa is also an early biomarker. In one embodiment of the invention, the method identifies the presence of a 6.4 kDa protein. In another embodiment, the method identifies the presence of a 28.5 kDa protein. In another embodiment, the method identifies the presence of a 44 kDa protein. In yet another embodiment of the invention, the method identifies the presence of a 33 kDa and a 67 kDa protein. These early biomarkers for assessing a change in renal status, which also are biomarkers of impaired renal status, are typically detected in a subject following a "renal event," and their detection is typically based upon mass and charge using the SELDI-TOF-MS technique or similar proteome analysis technique known in the art for protein expression profiling. As noted above, the 6.4 kDa protein, while an early biomarker for impaired or changing renal status, is detected only in conjunction with the intra-operative administration of aprotinin during cardio-pulmonary bypass surgery.

It is noted here that, due to the specific measuring technique used, the molecular weight in kilodaltons for each of the early biomarkers listed above could be reported in integers other than those specifically claimed herein, yet still be interpreted to be these proteins. As a non-limiting example, the 6.4 kDa protein may be reported within a range of 6.2 kDa to 6.6 kDa, such that, as used herein, the phrase "the 6.4 kDa protein" means a protein having a molecular weigh of about 6.4 kDa. Similarly, the 28.5 kDa protein is a protein having a molecular weight of about 28.5 kDa, the 33 kDa protein is a protein having a molecular weight of about 33 kDa, the 44 kDa protein is a protein having a molecular weight of about 44 kDa, and the 67 kDa protein is a protein having a molecular weight of about 67 kDa. As another example, in FIGS. 1A, 1B, 2A and 2B the measurements of the 67 kDa protein fall within a range of between about 65 to about 67 kilodaltons. Similarly, the measurements of the 44 kDa protein fall within a range of between about 43 to about 45 kilodaltons. Thus, while stated to be the 44 kDa protein, this protein could be reported by others to be of a molecular weight close to, but not exactly, 44 kDa.

In addition to the proteins identified by molecular weight, by standard proteomic profiling at 2 hours post-CPB, four novel urinary biomarkers for the early prediction of ARF have been identified: aprotinin, alpha-1-microglobulin (A1M), alpha-1-acid-glycoprotein (A1AG), and microalbumin. Like the 6.4 kDa protein, urinary aprotinin, while an early biomarker for impaired renal status, is detected only in conjunction with the intra-operative administration of aprotinin during cardio-pulmonary bypass surgery. Standard downstream assays (ELISA or nephelometry) are available for each of these proteins, and each one is a robust biomarker.

The invention first utilized a genome-wide interrogation strategy to identify kidney genes that are induced very early after ischemia in animal models, whose protein products might serve as novel biomarkers for the initiation phase of ARF. The 28.5 kDa protein biomarker detected by the preferred assay technique of this invention, i.e. proteomics, is the lipocalin alpha-1-microglobulin (A1M). Previously this 28.5 kDa biomarker, which was detected using SELDI-TOF-MS technology, was believed to be neutrophil gelatinase-associated lipocalin (NGAL), but conventional laboratory methods have confirmed that the biomarker is MM. This was surprising, since NGAL has previously been identified as one of the most dramatically up-regulated genes and proteins in the kidney after ischemia. Nevertheless, the 28.5 kDa protein, now confirmed to be A1M, was easily detected in the urine early shortly after a renal event, i.e. ischemic renal injury undergoing cardiac surgery. The invention thus provides an improved method of detecting early biomarkers of impaired renal status in humans.

An effective renal tubular cell injury biomarker, also known as a biomarker of impaired renal status, is typically a secreted protein, whereby it can be excreted by the kidney into the urine or transported within the blood serum. An effective biomarker of impaired renal status is also typically a protease-resistant protein, such as NGAL, however a biomarker of impaired renal status can also be a protease-sensitive protein, such as A1M, so long as stable fragments of the protein can be detected in the urine or in the blood serum. Identification of A1M by proteomics requires digestion with proteolysis and identification of peptide fragments. A1M is the 28.5 kDa biomarker, and an important immediate biomarker for renal tubular cell injury (which will also be referred to as biomarker of impaired renal status). A1M can appear in the urine within 2 hours of the onset of renal tubular cell injury. An immediate biomarker of impaired renal status can, as in the case of A1M, be present in the urine of a subject almost immediately after the onset of renal tubular cell injury. The biomarker of impaired renal status can also be an early-onset biomarker of impaired renal status that can appear within the first 24 hours, more typically within the first 6 hours, of the onset of renal tubular cell injury. As such, the 28.5 kDa protein A1M is also an example of an early-onset biomarker of impaired renal status.

The biomarker of impaired renal status can be an ischemic renal injury biomarker (IRI biomarker), a nephrotoxic renal injury biomarker (NRI biomarker), or a mixture thereof. The method of the invention can be used to detect the onset of renal tubular cell injury, and to monitor the treatment thereof, for a wide variety of events that can include all varieties of diminished blood supply to the kidneys, impaired heart function, surgical procedures, patients in intensive care units, and the administration of pharmaceuticals, radio contrast dyes, or other medicament substances to a subject. The renal tubular cell injury causing impaired renal status can be an ischemic renal injury, a nephrotoxic renal injury, or other injury that affects the tubular cells of the kidney. The event can include administration or ingestion of a large and wide variety of nephrotoxins, including, but not limited to cancer chemotherapy (cisplatin, cyclophosphamide, isosfamide, methotrexate), antibiotics (gentamicin, vancomycin, tobramycin), antifungal agents (amphotericin), anti-inflammatory agents (NSAIDs), immunosuppressants (cyclosporine, tacrolimus), and radio contrast agents. The method can be used to evaluate the nephrotoxicity of both newly-developed and well-known compounds.

The invention also provides a method for assessing the extent of impaired renal status based on a proportional relationship between the extent of injury, which can range from the very early onset of renal tubular cell injury to clinical ARF, with the quantity of early biomarker proteins present in the urine, blood serum, or other isolatable body fluid of the subject. The invention provides a means for a clinician to estimate the degree of impaired renal status at an initial assessment, and to monitor the change in status of the injury (worsening, improving, or remaining the same) based on the detected level of biomarkers of impaired renal status in the urine, blood serum, or other isolatable body fluid using the SELDI-TOF-MS technique or a similar proteomics technique for obtaining information on protein identity, protein-protein interaction, the level of protein expression, or protein expression profiling.

Typically, the clinician would establish a protocol of collecting and analyzing a quantity of fresh blood and/or urine samples from the patient at selected intervals. Typically the sample is obtained intermittently during a prescribed period. The period of time between intermittent sampling may be dictated by the condition of the subject, and can range from a sample each 24 hours to a sample taken continuously, more typically from each 4 hours to each 30 minutes. If the sample taken is a blood sample, then a serum sample is then typically isolated from the blood sample by well known means.

Using the methods and techniques described herein, both a qualitative level of the biomarker of impaired renal status present in the urine and/or serum can be analyzed and estimated, and a quantitative level of biomarker of impaired renal status present can be analyzed and measured. The clinician would select the qualitative method, the quantitative method, or both, depending upon the status of the patient. For blood samples, the quantity of blood serum to be collected is typically less than 1 milliliter (ml), and more typically less than 10 microliters (μl). A typical sample can range from about 1 μl to about 1 ml. Typically the larger quantities of a blood serum sample (about 1 ml) are used for quantitative assays. Typically, these small levels of serum are easily and readily available from clinical subjects who are either prone to developing ARF, or have developed ARF.

Once an indication of impaired renal status, including renal tubular cell injury or acute renal failure, has been detected and intervention and treatment of the disease or condition has commenced, the clinician can employ the method of the invention to monitor the progress of the treatment or intervention. If a treatment or surgery that might cause renal tubular cell injury is planned, the clinician can obtain a pre-treatment sample of urine, blood serum, or other isolatable body fluid from the subject to determine a baseline biomarker value for that individual. Typically, one or more subsequent post-treatment samples will be taken and analyzed for the presence of the biomarker of impaired renal status as the treatment of the renal injury commences and continues. If a baseline value was obtained, these post-treatment values can be compared to the baseline value to determine the relative condition of the patient. The treatment can be continued until the presence of the biomarker of impaired renal status in subsequent post-treatment samples either returns to baseline value or is no longer detected. As the treatment and intervention ameliorate the condition, the expression of biomarker of impaired renal status and its presence in the subject samples will be correspondingly reduced. The degree of amelioration will be expressed by a correspondingly reduced level of biomarker of impaired renal status, such as the 28.5 kDa protein (A1M), detected in a sample. As the renal injury nears complete healing, the method can be used to detect the return to baseline levels or the complete absence of the biomarker of impaired renal status, signaling the completion of the course of treatment.

Since biomarkers of impaired renal status can be easily detected within 2 hours of the renal injury or nephrotoxic treatment, the present invention using SELDI-TOF-MS, or an equivalent assay for rapidly detecting and characterizing proteins present at very low levels in a body fluid sample, is suitable for use as an early-onset diagnostic. Biomarker testing of urine, serum or other body fluid samples from a subject can begin within 30 minutes of a suspected injury, since biomarkers of impaired renal status begin to appear at low levels and continues to rise thereafter. Therefore, it is also of great value to initiate testing for biomarkers at any time within 2 hours of a suspected injury. Furthermore, it is of value to test at any other time during the first 24 hours following a suspected injury, since Biomarkers of impaired renal status can be highly reliable and easily measured markers of injury that appear in the urine and serum before changes in other parameters, such as creatinine, can be detected. The most highly preferred course of biomarker testing is to collect samples at intervals throughout the course of treatment to monitor real time changes in renal health status.

In one embodiment of the present invention, Surface-Enhanced Laser Desorption/Ionization Time-of-Flight Mass Spectrometry (SELDI-TOF-MS) technology was used to identify biomarker patterns that predict impaired renal status and disease in patients undergoing open heart surgery. In particular, this technology was used with infants and children with congenital heart disease who were undergoing cardiac surgery. This population may be especially vulnerable to developing ARF since many children require multiple surgeries for step-wise repair of complex congenital anomalies. However, these children are also unique, since confounding co-morbid conditions such as advanced age, atherosclerotic vascular disease and diabetes are usually absent, rendering them an ideal patient group for examination of biomarkers as predictors of early ischemic renal injury and/or impaired renal status.

Therefore, a homogeneous population of patients with no confounding variables was studied, in whom the only conceivable renal insult would be the result of ischemia-reperfusion injury following cardio-pulmonary bypass (CPB). None of the patients studied encountered intra-operative hypotension or significant peri-operative cardiac events. To minimize intra- and post-operative volume depletion, all patients received 80-100% of their maintenance fluid requirements during and after surgery, and their hematocrits were maintained at approximately 35%.

Acute renal injury has typically been defined as a sudden decrease in renal function resulting in an inability to maintain fluid and electrolyte balance and to excrete nitrogenous wastes. Serum creatinine is a conventional biomarker. In the absence of functioning kidneys, serum creatinine concentration will increase daily by as much as 1-1.5 mg/dL. Spot urine samples were collected at baseline and at two and six hours following CPB. When the CPB time exceeded 2 hours, the first post-operative urine sample was obtained at the end of CPB, and this sample was considered as the 2-hour collection. Samples were centrifuged at 2,000 g for 5 minutes, and the supernatants stored in aliquots at −80° Celsius. Serum creatinine was measured at baseline, and routinely monitored in these critically ill children at least twice a day in the immediate post-operative period, and then at least daily beyond post-operative day three. The primary outcome variable was the development of acute renal injury, defined as a 50% or greater increase in serum creatinine from baseline. Other variables obtained included age, gender, race, bypass time, urine output, urinalysis, and urine creatinine.

The measurement of urinary biomarkers in patient samples provides information that diagnosticians can correlate with a probable diagnosis of acute renal injury or a negative diagnosis (e.g., normal or injury-free). The biomarkers are characterized by molecular weight and/or charge. The biomarkers were resolved from other proteins in a sample by using an assay for rapidly detecting and characterizing proteins present at very low levels in a body fluid sample, typically the SELDI-TOF-MS technology (i.e. the ProteinChip® Biomarker System), in which the surface of the mass spectrometry probe comprises adsorbents that bind the biomarkers.

EXPERIMENTAL

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Equal volumes (1 μl) of urine were diluted 1:5 with sodium phosphate (pH 6) buffer, and 5 μl was spotted onto an NP20 protein array chip. Each spot was washed with distilled water, and a saturated sinapinic acid solution was used as matrix. The low intensity spectra were obtained with the laser set at an intensity of 145 and the high intensity spectra with the laser set at 195. The resulting spectra were calibrated using All-in-1 peptide/protein standards.

Example 2

To confirm the changes in urinary proteins observed by SELDI-TOF-MS, equal levels of samples were subjected to SDS-PAGE. Briefly, 25 μl urine samples were dissolved in an equal volume of 2×SDS-PAGE loading buffer, boiled for 10 minutes, loaded on a 10-20% Tris-Tricine gel, subjected to electrophoresis, and stained with Coomassie Blue. All values are mean±SE. SAS version 8.2 was used for statistical analysis of patient characteristics and clinical outcomes. The Mann-Whitney rank sum test was used to compare continuous variables, and Fisher's exact test was used to compare categorical variables.

Employed Method: The Biomarker Wizard (Ciphergen) was employed for initial clustering and descriptive statistics. Ciphergen Express software was used for hierarchical clustering and to generate Receiver Operating Characteristic (ROC) curves. The area under the curve was calculated to provide a measure of robustness for each biomarker. An area under the curve of 0.5 is considered no better than expected by chance, whereas a value of 1.0 signifies a perfect biomarker. Biomarker Pattern Software, an implementation of the Classification and Regression Tree algorithm, was utilized to generate predictive models for ARF based on multiple biomarkers. A 'p' value of <0.05 was considered significant.

Example 3

The primary outcome of acute renal injury, defined as a 50% or greater increase in serum creatinine from baseline, occurred in 15 of 60 consecutive patients, yielding an incidence rate of 25%. Out of these, 5 patients displayed an increase in serum creatinine in the 24-48 hours after CPB, but in the other 10 patients the increase was further delayed to the 48-72 hour period after CPB. Thus, the diagnosis of acute renal injury using currently accepted clinical practices could be made only days after the inciting event. Based on the primary outcome, patients were classified into "control" and acute renal injury or "ARF" groups.

Comparisons were made between the ARF group (n=15) and age- and gender-matched controls (n=15). There were no significant differences between the two groups in ethnic origin, hourly urine output, urine creatinine, or urine specific gravity measurements at baseline. Patients in the ARF group encountered longer cardio-pulmonary bypass times compared with those who did not develop ARF (160±15 versus 74±9 min, p<0.05). Cardiac surgery did not result in a significant difference in urine creatinine, urine specific gravity, or hematuria in either the control or the ARF group.

Figure 1B:
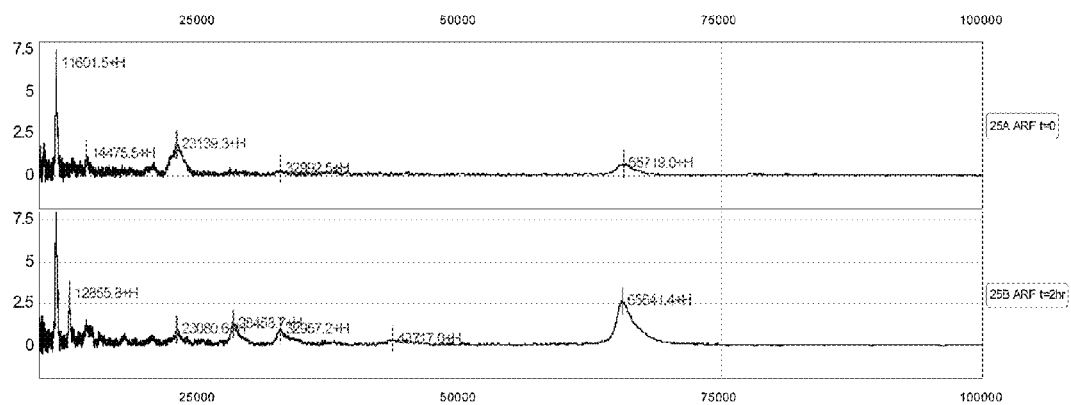
FIG. 1B is a graph showing representative SELDI-TOF-MS spectra of urine proteins in the 10,000-100,000 kDa range obtained from patients in the ARF group at baseline (top panel) and at 2 hours post-CPB (bottom panel).

Equal volumes of urine from control and ARF groups were analyzed by SELDI-TOF-MS, since urine creatinine and specific gravity did not change significantly in the pre-versus post-operative samples, precluding the need to normalize measurements for urine concentrations. Representative samples of spectra obtained are shown in FIGS. 1A, 1B, 2A and 2B. FIG. 1A shows proteins in the 2,000-10,000 kDa range, and FIG. 1B shows proteins in the 10,000-100,000 kDa range, obtained at baseline (top panel) and 2 hours post CPB (bottom panel).

Figure 2A:
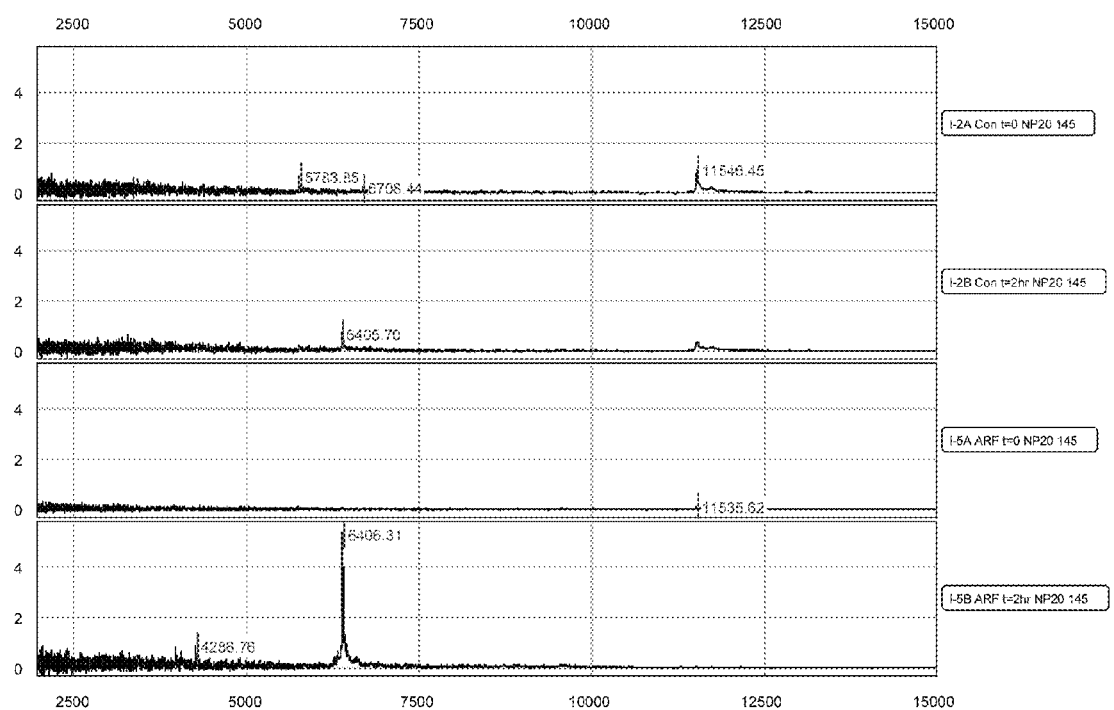
FIG. 2A is a graph showing representative SELDI-TOF-MS spectra of urine proteins in the 2,000-15,000 kDa range obtained from control patients at baseline (top panels) and 2 hours post CPB (second panels), and from patients in the ARF group at baseline (third panels) and 2 hours post CPB (bottom panels).
Figure 2B:
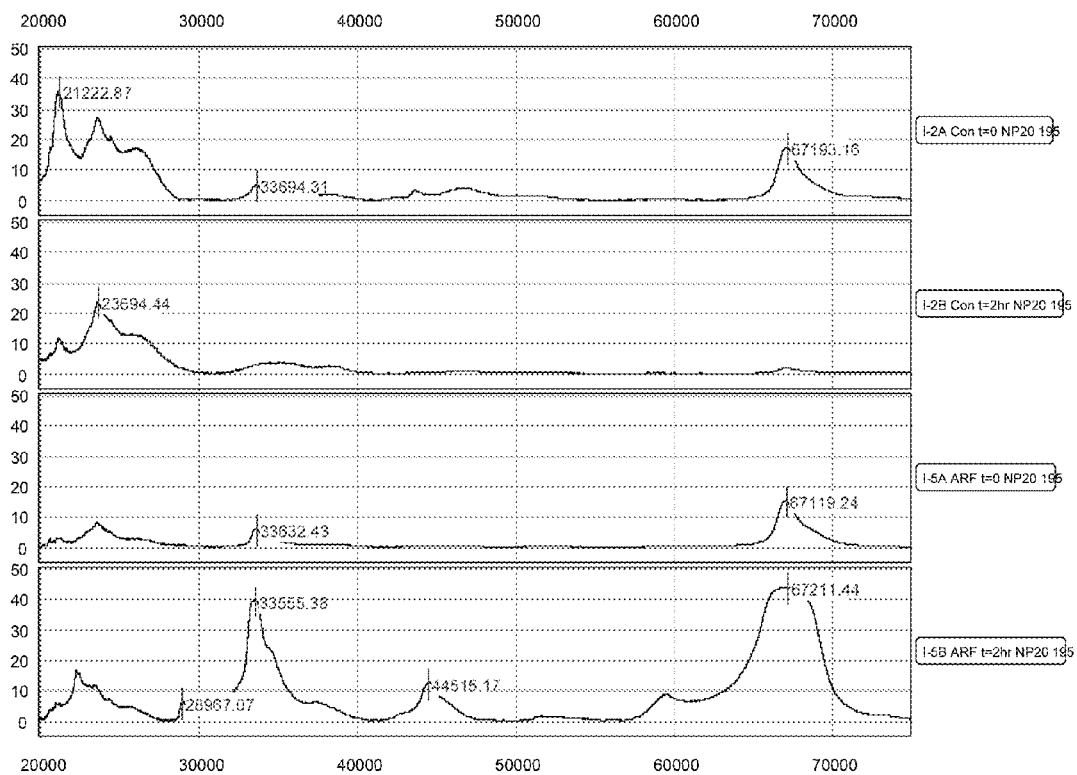
FIG. 2B is a graph showing representative SELDI-TOF-MS spectra of urine proteins in the 20,000-75,000 kDa range obtained from control patients at baseline (top panels) and 2 hours post CPB (second panels), and from patients in the ARF group at baseline (third panels) and 2 hours post CPB (bottom panels).

SELDI-TOF-MS analysis of the ARF group at baseline (t=0) versus at 2 hours post-CPB (t=2 h) and at 6 hours post CPB (not shown) consistently showed a marked and statistically significant enhancement of protein biomarkers with a mass-to-charge ratio (m/z) of 6.4, 28.5, 44 and 67 kDa. The sensitivity and specificity of the 28.5, 44 and 67 kDa biomarkers for the early prediction/determination of ARF at 2 hours following CPB was 100%. The receiver operating characteristic curves revealed an area under the curve of 0.98. Several additional protein species (for example, m/z of 7.3 and 8.9 in FIG. 1A and 12.8 in FIG. 1B) were also enhanced in the ARF group at 2 hours post CPB, but these changes did not achieve statistical significance. The same biomarkers with m/z of 6.4, 28.5, 44 and 67 kDa were also significantly enhanced when comparing control versus ARF groups at 2 hours post-CPB (FIGS. 2A and 2B).

Figure 3:
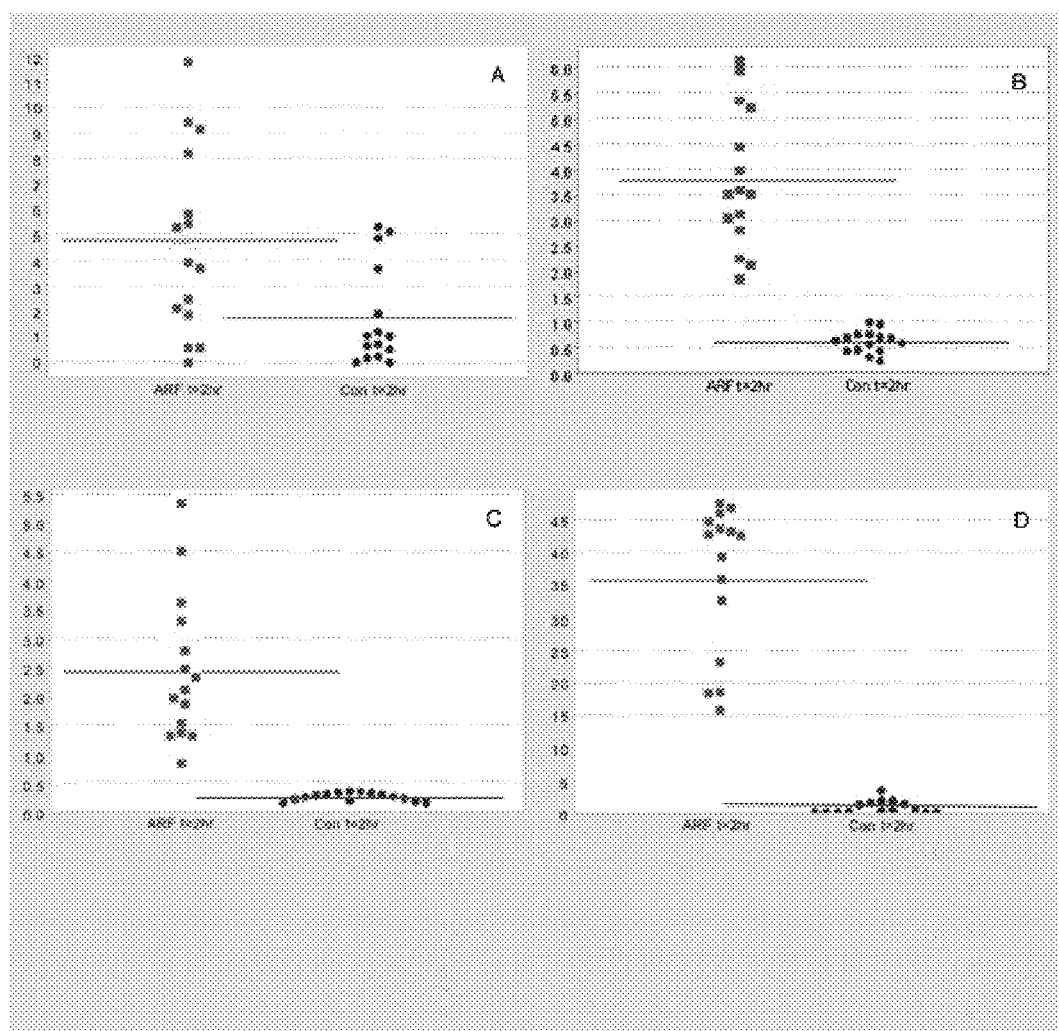
FIG. 3 is a graph showing scatter plots of peak intensities for each of the biomarkers measured at 2 hours post CPB in the control and ARF groups.

The scatter plots of peak intensities for each of statistically significant biomarkers (m/z of 6.4, 28.5, 44 and 67 kDa) is illustrated in FIG. 3. Biomarkers were measured at 2 hours after CPB in the control (circles, n=15) and ARF (squares, n=15) groups. The horizontal line represents the mathematical mean intensity value. A=6.4 kDa, B=28.5 kDa, C=44 kDa, and D=67 kDa. The biostatistical analyses of the results are shown in Tables 1-4.

TABLE 1

| | ARF (t = 0) versus ARF (t = 2 hours) | | |
|---|---|---|---|
| M/Z (kDa) | Fold increase in average peak intensity | p-value | Area under ROC Curve |
| 6.4 | 24.1 | <0.00006 | 0.93 |
| 28.5 | 4.8 | <0.000005 | 0.98 |
| 44 | 12.3 | <0.00001 | 0.95 |
| 67 | 2.2 | <0.00017 | 0.90 |

Table 1. Biostatistical analysis of increases in peak biomarker intensities in the ARF group at baseline (t = 0) versus 2 hours post CPB (t = 2 h).

TABLE 2

| | ARF (t = 2 hours) versus Control (t = 2 hours) | | | | |
|---|---|---|---|---|---|
| M/Z (kDa) | Fold increase in avg. peak intensity | p-value | Sensitivity (%) | Specificity (%) | Area under ROC Curve |
| 6.4 | 2.6 | <0.017 | 80 | 88 | 0.77 |
| 28.5 | 4.8 | <0.000003 | 100 | 100 | 0.98 |
| 44 | 12.3 | <0.000003 | 93 | 100 | 0.98 |
| 67 | 42.1 | <0.000003 | 100 | 100 | 0.98 |

Table 2. Biostatistical analysis of increases in peak biomarker intensities in the ARF versus control group at 2 hours post CPB.

TABLE 3

Control (t = 0) versus ARF (t = 0 hours)

| M/Z (kDa) | Fold increase in average peak intensity | p-value | Area under ROC Curve |
|---|---|---|---|
| 6.4 | 1.01 | 0.61 | 0.44 |
| 28.5 | 0.96 | 0.27 | 0.37 |
| 44 | 0.87 | 0.29 | 0.58 |
| 67 | 0.75 | 0.08 | 0.31 |

Table 3. Biostatistical analysis of differences in peak biomarker intensities in the ARF versus control group at baseline (t = 0).

TABLE 4

Control (t = 0) versus Control (t = 2 hours)

| M/Z (kDa) | Fold increase in average peak intensity | p-value | Area under ROC Curve |
|---|---|---|---|
| 6.4 | 9.01 | 0.0013 | 0.85 |
| 28.5 | 0.79 | 0.07 | 0.31 |
| 44 | 0.36 | 0.00003 | 0.07 |
| 67 | 0.04 | 0.000003 | 0.02 |

Table 4. Biostatistical analysis of increases in peak biomarker intensities in the ARF group at baseline (t = 0) versus 2 hours post CPB (t = 2 h).

It should be noted that the serum creatinine in the ARF group of patients did not increase until day 2-3 after surgery. In the same cohort, SELDI-TOF-MS analysis of urine obtained within 2 hr of CPB revealed a dramatic increase in peak intensity of all four biomarkers (Tables 1 and 2). The sensitivity and specificity of the 28.5, 44 and 67 kDa biomarkers for the early prediction/determination of ARF at 2 hours was 100% (Table 2). The receiver operating characteristic curves for these biomarkers revealed an area under the curve of 0.98, indicative of extremely powerful biomarkers (Table 2). No differences in these biomarkers were detected in control versus ARF urines at baseline (Table 3). Furthermore, patients in the control group displayed only a small (although statistically significant) increase in the 6.4 kDa urinary biomarker, and no increase (but rather a decrease) in peak intensity of the 28.5, 44 and 67 kDa biomarkers at 2 hr post-CPB (Table 4).

Example 4

Figure 4:
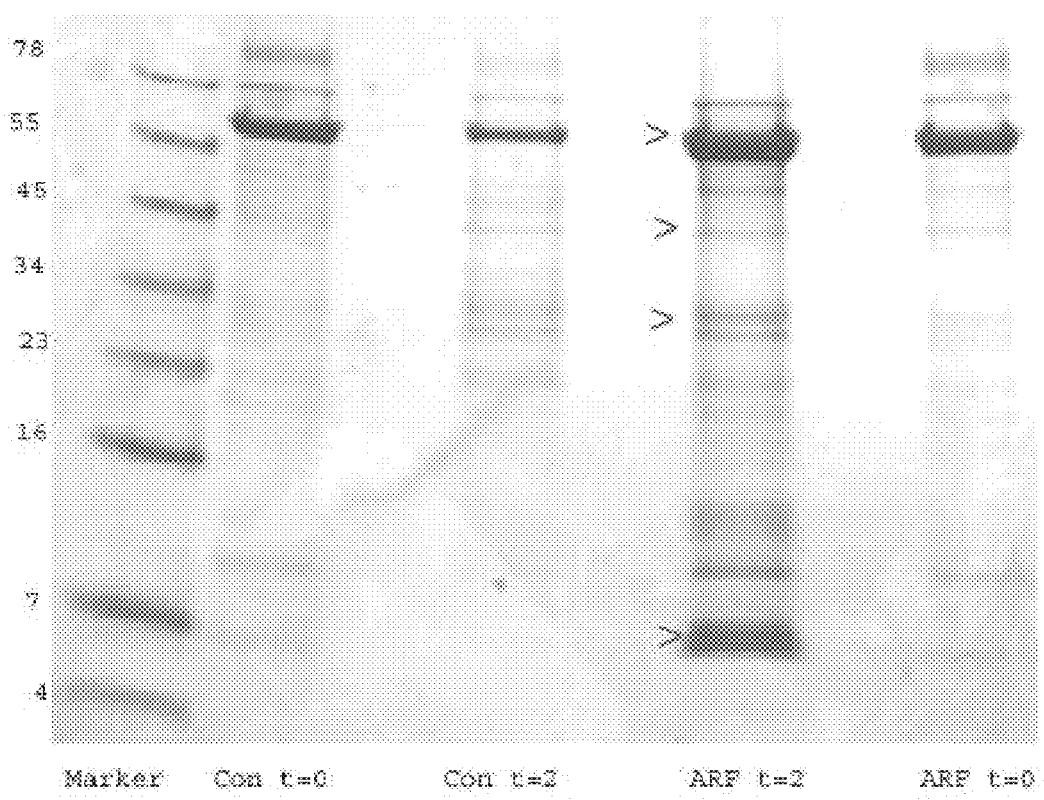
FIG. 4 is a representative gel of urine samples obtained from control and ARF patients at baseline (t=0) and 2 hours post CPB (t=2).

In order to confirm the changes in urine protein detected by SELDI-TOF-MS, samples were analyzed by gel electrophoresis and Coomassie Blue staining. A representative gel is shown in FIG. 4. Marked up-regulation of the 6.4 and 67 kDa biomarkers was easily identified in the ARF group at 2 hours post-CPB (t=2 h), as predicted by the SELDI-TOF-MS measurements. Changes in the excretion of the 28.5 and 44 kDa biomarkers were also detectable but less apparent. Changes in several additional protein bands such as the 12.8 species were also noted. As previously mentioned, these species were also enhanced by SELDI-TOF-MS analysis, but did not reach statistical significance.

At least four distinct biomarkers that are not related to administration of aprotinin during cardio-pulmonary bypass but are enhanced within 2 hours of a renal event such as ischemic injury and highly predictive of subsequent ARF occurring days after such a renal event have been identified by the present invention. These include the 28.5 kDa protein, the 33 kDa protein, the 44 kDa protein, and the 67 kDa protein. The SELDI-TOF-MS method is sensitive, reproducible, rapid (with a turnaround time of only 90 minutes), and non-invasive (requiring only microliter quantities of urine). The 6.4 kDa protein, in contrast, while also an early biomarker for impaired renal status, is detected only in conjunction with the intra-operative administration of aprotinin during cardio-pulmonary bypass surgery.

Data was acquired from a homogeneous cohort of children subjected to renal ischemia-reperfusion injury during surgical correction of congenital cardiac disease. These patients were devoid of common co-morbid variables such as atherosclerotic vascular disease, diabetes, and nephrotoxin use, all of which can confound and vitiate the identification of early biomarkers for ischemic acute renal injury. All subjects started with normal kidney function and normal patterns of the urinary proteins. This study design allowed for the determination of the precise timing of alterations in the urinary proteome following CPB. Thus, urinary proteomic analysis represents a powerful method for the early identification of biomarkers for determination of acute renal injury, preceding any increase in serum creatinine by 1-3 days.

Two independent techniques for the detection of changes in the urinary proteome following cardiac surgery are described herein, namely SELDI-TOF-MS and SDS-PAGE followed by Coomassie Blue staining. Marked up-regulation of at least two biomarkers (6.4 and 67 kDa) was easily identified in the ARF group at 2 hours post-CPB by both methods. However, the SELDI-TOF-MS offers several advantages over SDS-PAGE. First, changes in the excretion of the 28.5 and 44 kDa biomarkers were easily detectable by SELDI-TOF-MS, but much less apparent by SDS-PAGE. Second, SELDI-TOF-MS methods provide quantitative measures of changes in biomarker excretion which can be followed over time, whereas the information gleaned from SDS-PAGE is purely qualitative. Third, SELDI-TOF-MS can provide rapid results in a clinical situation where time is of the essence, whereas SDS-PAGE followed by staining and de-staining requires several hours. Fourth, the SELDI-TOF-MS results were fully reproducible in all patients who developed ARF, while SDS-PAGE results were prone to variations.

The methods of the present invention further include managing subject treatment based on the status. The invention also provides for such methods where the biomarkers (or specific combination of biomarkers) are measured again after subject management. In these cases, the methods are used to monitor the renal status of the patient, e.g., the response to treatment. Because of the ease of use of the methods and the lack of invasiveness of the methods, the methods can be repeated after each treatment the patient receives. This allows the physician to follow the effectiveness of the course of treatment. If the results show that the treatment is not effective, the course of treatment can be altered accordingly. This enables the physician to be flexible in the treatment options.

Urinary proteomic profiling has uncovered a distinctive acute renal failure (ARF) "fingerprint" that includes the five distinct biomarkers of impaired renal status listed above, namely a 6.4 kDa protein, a 28.5 kDa protein, a 33 kDa protein, a 44 kDa protein, and a 67 kDa protein. It is highly likely that not just one biomarker, but rather a collection of strategically selected biomarkers of impaired renal status will comprise an "ARF Panel" for the early prediction of impaired renal status. Identification and characterization of novel predictive ARF biomarkers is critically important. The five distinct biomarkers of impaired renal status were revealed by careful high resolution analysis using standard conditions (NP-20 chip, pH 6, 5% BSA block), that are markedly enhanced within 2 hours of cardio-pulmonary bypass (CPB) in patients who subsequently developed ARF (defined as a 50% or greater increase in serum creatinine). These include species of m/z of 6.4, 28.5, 33.0, 44.0, and 67.0 kDa.

Urinary proteins were separated by SDS-PAGE, and the individual protein bands excised and digested with trypsin. Single MS and MS/MS spectra of peptide fragments were acquired on a tandem mass spectrometer (Applied Biosystems Q-Star XL) equipped with a PCI-1000 ProteinChip Interface. The CID spectra were submitted to a database-mining tool Mascot (Matrix Sciences) for identification. Urinary protein sequence data identified the following: aprotinin at 6.4 kDa, alpha-1-microglobulin (A1M) at 28.5 kDa, alpha-1-acid-glycoprotein (A1AG) at 44 kDa, and albumin at 67 kDa. Standard downstream assays (ELISA or nephelometry) are available for each of these proteins, and each one is a robust biomarker. Nephelometry is a standard clinical chemistry assay to measure concentration of substances in urine or blood or any body fluid, and is used to quantitate proteins by analyzing increases in turbidity, as measured by increasing scatter of laser light. The interaction of specific antibodies in the reagent with the antigen from the sample results in the formation of antigen-antibody complexes which are rendered insoluble by the presence of precipitating reagents. Most modern nephelometers compare the rate of formation of antigen-antibody complexes (determined by computer analysis of laser light scatter data) to that of known antigenic standards in order to measure precisely the protein antigens present in moderate concentrations.

Urinary proteomic profiling employed in the present invention has uncovered a distinctive acute renal failure (ARF) "fingerprint" that includes the five distinct biomarkers of impaired renal status listed above, namely a 6.4 kDa protein, a 28.5 kDa protein, a 33 kDa protein, a 44 kDa protein, and a 67 kDa protein. It is highly likely that not just one biomarker, but rather a collection of strategically selected biomarkers of impaired renal status will comprise an "ARF Panel" for the early prediction of impaired renal status. Identification and characterization of novel predictive ARF biomarkers is critically important. The five distinct biomarkers of impaired renal status were revealed by careful high resolution analysis using standard conditions (NP-20 chip, pH 6, 5% BSA block), that are markedly enhanced within 2 hours of cardiopulmonary bypass (CPB) in patients who subsequently developed ARF (defined as a 50% or greater increase in serum creatinine). These include species of m/z of 6.4, 28.5, 33.0, 44.0, and 67.0 kDa.

The 33 kDa species has been identified as a doubly protonated form of albumin, and has the same biomarker qualities of the 67 kDa species of albumin. A brief description of the remaining identified proteins and results of downstream confirmatory studies are presented below.

6.4 kDa Protein/Aprotinin. The 6.4 kDa protein has proven to be unique to this group, because it was found to appear only in patients with impaired renal status who were (1) post cardio-pulmonary bypass (CBP) surgery and (2) who also received the medication aprotinin during CBP. Aprotinin is an approved medication that is commonly used to limit blood loss during cardiac surgery. However, a recent landmark study has shown that the use of aprotinin is associated with a doubling in the risk of kidney failure. Prospective assays were performed for a 6.4 kDa protein that was suspected to be urine aprotinin in 30 patients following CPB (15 ARF and 15 controls), using proteomics. Urinary aprotinin levels (i.e. presence of a 6.4 kDa protein, detected by proteomics and later confirmed to be aprotinin by more conventional means), at 2 hours post-CPB surgery were significantly greater (by 2.6 fold) in patients who subsequently developed ARF (2-4 days later). These results document the validity of an approach towards identifying novel urinary biomarkers for the early prediction of ARF, and have revealed aprotinin as a highly promising candidate for the putative "ARF panel."

The rapid detection of elevated levels of the 6.4 kDa biomarker in the urine of patients, both during and immediately post-CBP surgery using proteomics, is likely the result of intra-operative administration of aprotinin in too high amounts for the patient. Thus it may be that overzealous administration of aprotinin to control blood loss during CPB surgery can lead to impaired renal status post-operatively. The method disclosed herein of detecting a 6.4 kDa protein, either during or shortly post-CPB, using proteomics provides an early indicator of impending impaired renal status. In addition, later confirming (via conventional laboratory techniques other than proteomics) the presence of urinary aprotinin in patients during or post-CPB can be invaluable for therapeutic decisions regarding the intra-operative dosing of this commonly used medication.

28.5 kDa Protein/Alpha-1-Microglobulin (A1M). A1M, also known as protein HC (for Heterogeneous Charge) is a low molecular weight glycoprotein produced primarily in the liver and kidney. It is a member of the lipocalin superfamily. Although much is now known of its structure and properties, the function and physiological role of A1M remains unclear. Very small levels of A1M are excreted in the normal urine, and a decrease in glomerular filtration results in increased levels of serum A1M. It has been suggested that A1M is also a tubular protein, and its urinary excretion is increased following tubular damage. A recent study has shown that patients with ARF who require renal replacement therapy display increased concentration of A1M in the urine early in the course of ARF. A prospective assay for urine A1M was performed on patient samples following CPB, using three independent assays: the SELDI-TOF-MS method, a standardized ELISA purchased from Immunodiagnostik, and a validated immunonephelometric test done on a Dade-Behring BN ProSpec apparatus. When compared to pre-operative levels, all three techniques reveal a consistent four to five-fold increase in urinary A1M that was detectable within 2 hours of CPB in 15 patients who subsequently developed ARF (defined as a 50% or greater increase in serum creatinine). This increase was sustained at 6 hours post CPB. Urinary A1M remained almost undetectable in 15 patients who did not develop ARF. These results document the validity of an approach towards identifying novel urinary biomarkers for the early prediction of ARF, and have revealed A1M as one more highly promising candidate for the putative "ARF panel."

44 kDa Protein/Alpha-1-Acid-Glycoprotein (A1AG). A1AG is an acute phase glycoprotein synthesized primarily in the liver. Very small levels are excreted in the normal urine. Its concentration in the serum is elevated during acute inflammatory conditions. Nothing is known about the urinary excretion of A1AG in disease states, although a recent publication has documented that exogenously administered A1AG protects against renal ischemia-reperfusion injury in animal models. Prospectively assays for urine A1AG were performed in patients following CPB, using three independent assays—SELDI-TOF, Western blots using monoclonal antibodies purchased from Abcam (ELISA assays are not commercially available), and a validated immunonephelometric test done on a Dade-Behring BN ProSpec apparatus. When compared to baseline levels, all three techniques reveal a consistent ten to twelve-fold increase in urinary A1AG that was detectable within 2 hours post-CPB in 15 patients who subsequently developed ARF (defined as a 50% or greater increase in serum creatinine). This increase was sustained at 6 hours post CPB. Urinary A1AG remains almost undetectable in patients who do not develop ARF. These results once again document the validity of an approach towards identifying novel urinary biomarkers for the early prediction of ARF, and have revealed A1AG as one more highly promising candidate for the putative "ARF panel."

67 kDa Protein/Microalbumin. Microalbuminuria is an established predictor for the development of diabetic nephropathy, but can also result from acute changes in microvascular permeability, such as acute inflammation and sepsis. A recent study has shown the predictive value of microalbuminuria for the development of multi-organ failure in medical ICU patients. Prospectively assays were performed for urine microalbumin in patients following CPB, using SELDI-TOF-MS and a validated immunonephelometric test done on a Dade-Behring BN ProSpec apparatus. The results reveal a consistent five to ten-fold increase in urinary microalbumin that was detectable within 2 hours of CPB in 10 patients who subsequently developed ARF (defined as a 50% or greater increase in serum creatinine). This increase was sustained at 6 hours post CPB. When compared to baseline levels, urinary microalbumin is only slightly increased in patients who do not develop ARF. These preliminary results once again document the validity of an approach towards identifying novel urinary biomarkers for the early prediction of ARF, and have revealed microalbumin as one more promising candidate for the putative "ARF panel."

Figure 5:
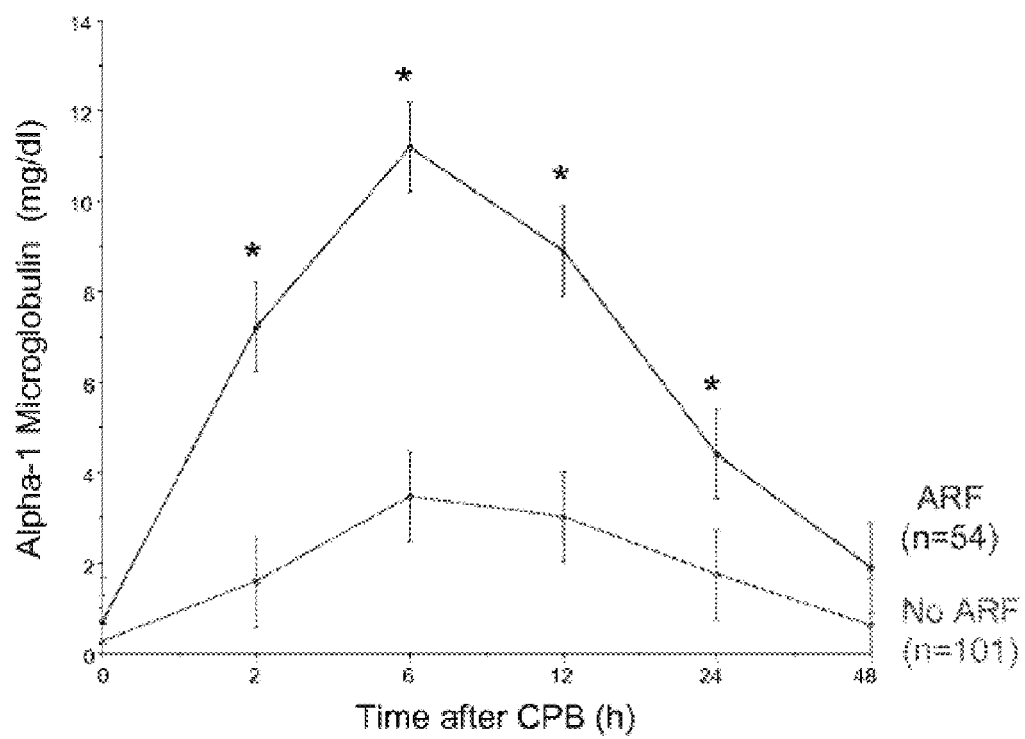
FIG. 5 is a graph showing urine alpha-1 microglobulin levels in ARF patients versus non-ARF patients at various times after cardio-pulmonary bypass, determined by quantitative nephelometry.

FIGS. 5-8 illustrate individual results for one of the four early biomarkers of impaired renal status which are elevated following a renal event. FIG. 5 shows urine A1M levels (in mg/dl) at various times after cardio-pulmonary bypass in 54 patients who subsequently developed ARF versus 101 patients who did not, determined by quantitative nephelometry. The initial rise in serum creatinine was detected only after 48 hours. At all post CPB time points examined except at 48 hours, urine A1M was significantly greater in subjects who developed ARF, as defined by a 50% increase in serum creatinine over baseline.

Figure 6:
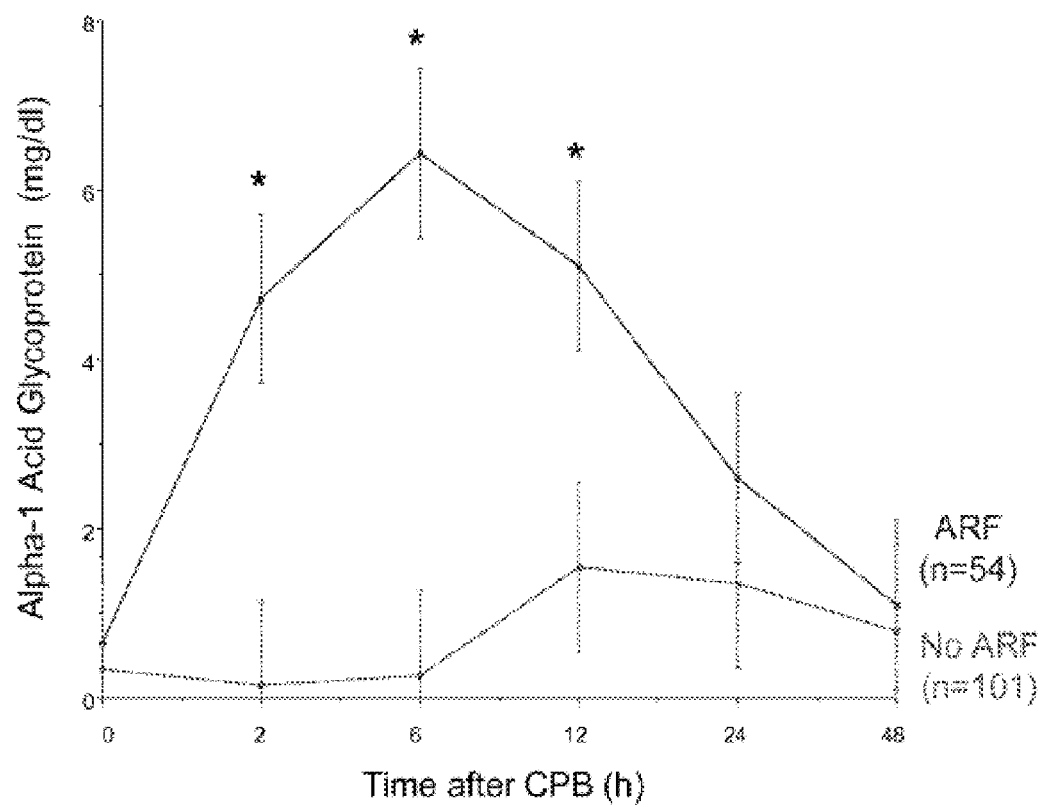
FIG. 6 is a graph showing urine alpha-1 acid glycoprotein levels in ARF patients versus non-ARF patients at various times after cardio-pulmonary bypass, determined by quantitative nephelometry.

FIG. 6 shows urine A1AG levels (in mg/dl) at various times after cardio-pulmonary bypass in 54 patients who subsequently developed ARF versus 101 patients who did not, determined by quantitative nephelometry. The initial rise in serum creatinine was detected only after 48 hours. At all post CPB time points examined except at 24 and 48 hours, urine alpha-1 acid glycoprotein was significantly greater in subjects who developed ARF, as defined by a 50% increase in serum creatinine over baseline.

Figure 7:
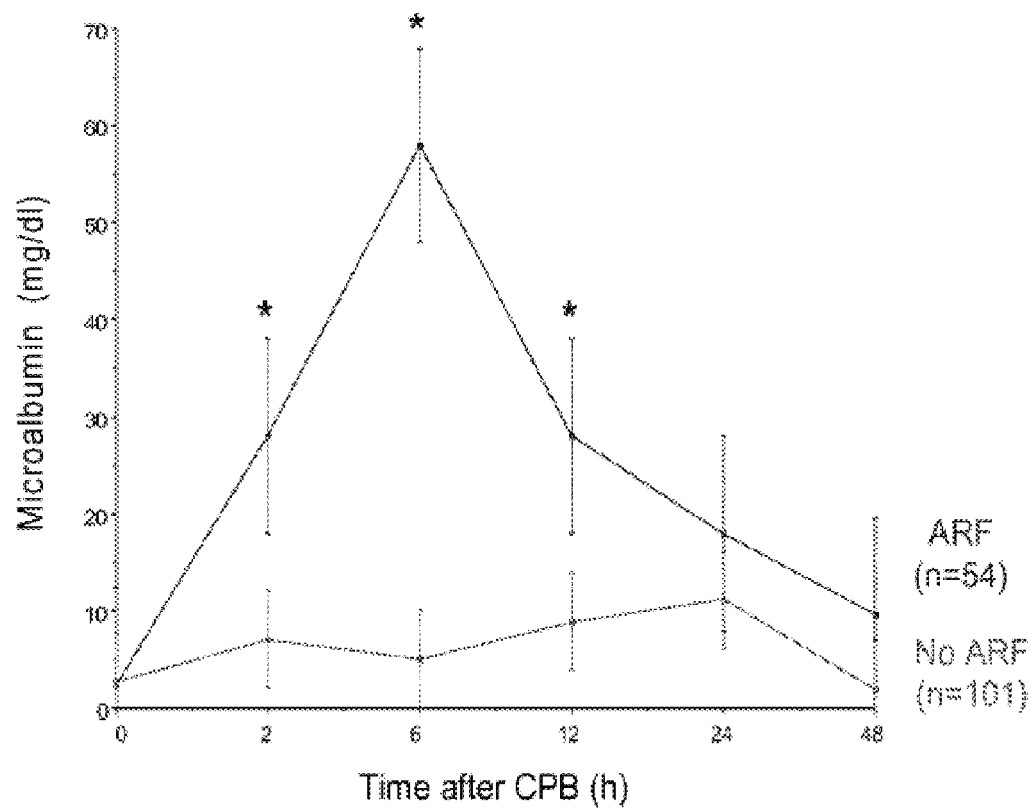
FIG. 7 is a graph showing urine microalbumin levels in ARF patients versus non-ARF patients at various times after cardio-pulmonary bypass, determined by quantitative nephelometry.

FIG. 7 shows urine microalbumin levels (in mg/dl) at various times after cardio-pulmonary bypass in 54 patients who subsequently developed ARF versus 101 patients who did not, determined by quantitative nephelometry. The initial rise in serum creatinine was detected only after 48 hours. At all post CPB time points examined except at 24 and 48 hours, urine microalbumin was significantly greater in subjects who developed ARF, as defined by a 50% increase in serum creatinine over baseline.

Figure 8:
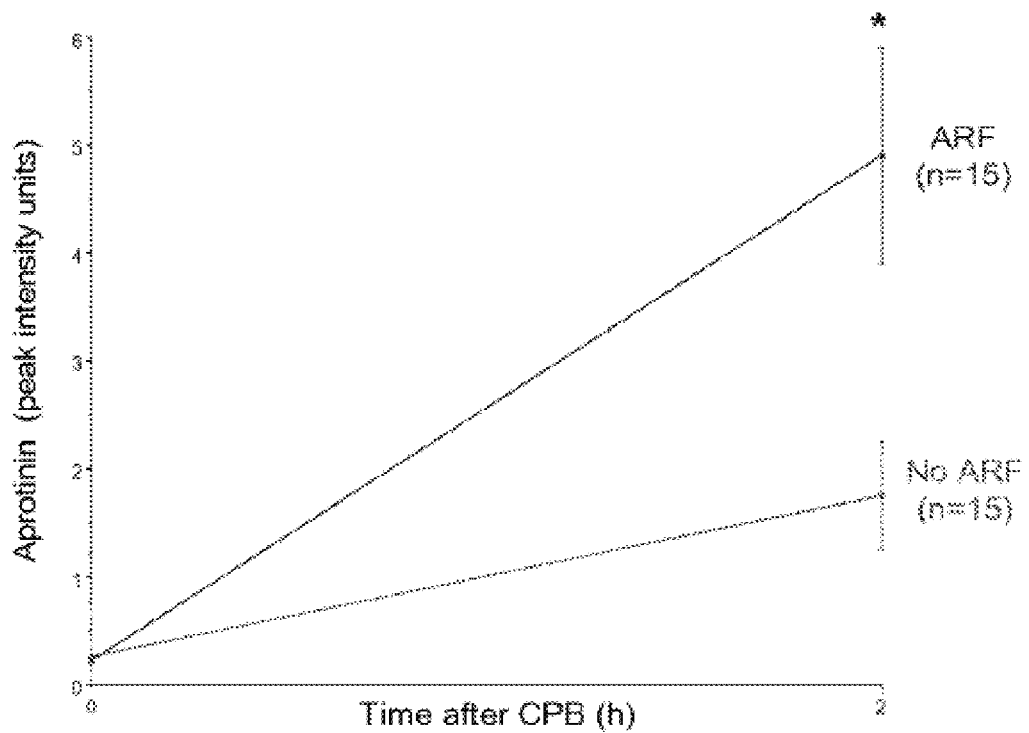
FIG. 8 is a graph showing urine aprotinin levels in ARF patients versus non-ARF patients at baseline and 2 hours after cardio-pulmonary bypass, determined by SELDI-TOF.

FIG. 8 shows urine aprotinin levels (in peak intensity units) at baseline and 2 hours after cardio-pulmonary bypass in 15 patients who subsequently developed ARF versus 15 patients who did not, determined by SELDI-TOF. The initial rise in serum creatinine was detected only after 48 hours. At 2 hours post CPB, urine aprotinin was significantly greater in subjects who developed ARF, as defined by a 50% increase in serum creatinine over baseline.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. A method for the detection of an early biomarker for assessing acute renal failure (ARF) following a renal event, the method comprising the steps of:
   a. analyzing the molecular weight of the proteins in a body fluid sample obtained from a mammalian subject following a renal event using proteome analysis; and
   b. identifying the presence of a combination of proteins consisting of a 6.4 kDa protein, a 28.5 kDa protein, a 33 kDa protein, a 44 kDa protein, and a 67 kDa protein, the presence of the combination serving as an early biomarker for assessing a change in renal status.

2. The method of claim 1, wherein the body fluid for the sample is selected from the group consisting of urine, blood, serum, plasma, saliva, lymph, cerebrospinal fluid, cystic fluid, ascites, stool, bile, and any other isolatable body fluid.

3. The method of claim 1, wherein the body fluid for the sample is isolated urine.

4. The method of claim 1, wherein proteome analysis is accomplished by the SELDI-TOF-MS technique.

5. The method of claim 1, wherein the protein is a 6.4 kDa protein.

6. The method of claim 1, wherein the protein is a plurality of proteins consisting of a 28.5 kDa protein, a 33 kDa protein, a 44 kDa protein, and a 67 kDa protein.

7. The method of claim 1, wherein the combination consists of a 33 kDa protein, a 67 kDa protein and combinations thereof.

8. A method for determining acute renal injury of a mammalian subject within 48 hours following a renal event, the method comprising the steps of:
   a. separating the proteins in a body fluid sample obtained from a mammalian subject at a time within 48 hours following a renal event by molecular weight using proteome analysis;
   b. identifying a combination of separated proteins based on the molecular weight of the separated protein, the combination consisting of a 6.4 kDa protein, a 28.5 kDa protein, a 33 kDa protein, a 44 kDa protein, and a 67 kDa protein; and
   c. comparing the level of each identified protein to a predetermined level thereof, the comparison providing a determination of the subject's renal status.

9. The method of claim 8, wherein the separated protein is a plurality of proteins consisting of a 28.5 kDa protein, a 33 kDa protein, a 44 kDa protein, and a 67 kDa protein.

10. The method of claim 8, wherein the body fluid for the sample is selected from the group consisting of urine, blood, serum, plasma, saliva, lymph, cerebrospinal fluid, cystic fluid, ascites, stool, bile, and any other isolatable body fluid.

11. The method of claim 8, wherein the body fluid for the sample is isolated urine.

12. The method of claim 8, wherein proteome analysis is accomplished by the SELDI-TOF-MS technique.

* * * * *